United States Patent
Park et al.

(10) Patent No.: US 11,992,471 B2
(45) Date of Patent: May 28, 2024

(54) REELIN/VEGF-C PRODUCTION/ACTIVATION PROMOTER AND SKIN EXTERNAL COMPOSITION USING THE SAME

(71) Applicant: AMOREPACIFIC CORPORATION, Seoul (KR)

(72) Inventors: Phil June Park, Yongin-si (KR); Hyunsoo Kim, Yongin-si (KR); Hyoung June Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 18/059,332

(22) Filed: Nov. 28, 2022

(65) Prior Publication Data

US 2023/0165816 A1    Jun. 1, 2023

(30) Foreign Application Priority Data

Nov. 29, 2021    (KR) ........................ 10-2021-0167441

(51) Int. Cl.
| | | |
|---|---|---|
| *A61K 31/185* | (2006.01) | |
| *A61K 9/00* | (2006.01) | |
| *A61K 47/02* | (2006.01) | |
| *A61K 47/12* | (2006.01) | |
| *A61K 47/36* | (2006.01) | |
| *A61K 47/46* | (2006.01) | |
| *A61P 29/00* | (2006.01) | |

(52) U.S. Cl.
CPC .......... *A61K 31/185* (2013.01); *A61K 9/0014* (2013.01); *A61K 47/02* (2013.01); *A61K 47/12* (2013.01); *A61K 47/36* (2013.01); *A61K 47/46* (2013.01); *A61P 29/00* (2018.01)

(58) Field of Classification Search
CPC .................................................. A61K 31/185
See application file for complete search history.

(56) References Cited

U.S. PATENT DOCUMENTS

| | | |
|---|---|---|
| 2005/0238679 A1 | 10/2005 | Biergiesser et al. |
| 2012/0245080 A1 | 9/2012 | Goolsbee et al. |
| 2015/0328137 A1 | 11/2015 | Nakamura et al. |

FOREIGN PATENT DOCUMENTS

| | | |
|---|---|---|
| JP | 6798149 B2 | 12/2020 |
| KR | 0162281 B1 | 12/1998 |
| KR | 10-0667038 B1 | 1/2007 |
| KR | 10-2018-0032581 A | 3/2018 |
| KR | 10-2135989 B1 | 7/2020 |
| WO | 2012/165610 A1 | 12/2012 |

OTHER PUBLICATIONS

Samira Boujendar, et al., "Taurine Supplementation of a Low Protein Diet Fed to Rat Dams Normalizes the Vascularization of the Fetal Endocrine Pancreas", Nutrient Requirements, American Society for Nutritional Sciences, Apr. 9, 2003, pp. 2820-2825.
Extended European Search Report dated Apr. 25, 2023 in Application No. 22209682.8.
Kirsi Narko et al., "Effect of inflammatory cytokines on the expression of the vascular endothelial growth factor-C", International Review of Experimental Pathology, 1999, vol. 80, pp. 109-112 (4 total pages).
Ursula Schmidt-Erfurth, "Nutrition and Retina", Developments in Ophthalmology, 2005, vol. 38, pp. 120-147 (30 total pages).
Yashodhara Sharma et al., "Nutrition for diabetic retinopathy: plummeting the inevitable threat of diabetic vision loss", European Journal of Nutrition, Mar. 3, 2017, vol. 56, pp. 2013-2027 (15 total pages).
Y. Su et al., "Taurine Improves Functional and Histological Outcomes and Reduces Inflammation in Traumatic Brain Injury", Neuroscience, 2014, vol. 266, pp. 56-65 (10 total pages).

*Primary Examiner* — Golam M Shameem
(74) *Attorney, Agent, or Firm* — Sughrue Mion, PLLC

(57) ABSTRACT

Provided are a reelin and/or VEGF-C production and/or VEGF-C activation promoter including a compound including a sulfonic acid group and an amino group as an active ingredient, and a skin external composition including the compound.

2 Claims, 3 Drawing Sheets

REELIN/VEGF-C PRODUCTION/ACTIVATION PROMOTER AND SKIN EXTERNAL COMPOSITION USING THE SAME

CROSS-REFERENCE TO RELATED APPLICATION

This application claims priority to and the benefit of Korean Patent Application No. 10-2021-0167441 filed in the Korean Intellectual Property Office on Nov. 29, 2021, the entire contents of which are incorporated herein by reference.

BACKGROUND

(a) Field of the Invention

This disclosure relates to a reelin and/or VEGF-C production and/or activation promoter and a skin external composition using the same.

(b) Description of Related Art

Edema refers to a condition that tissue fluid accumulates between cells of the body, and simply, a symptom of body swelling. This also may be caused by heart disease, kidney disease, or a blood circulation disorder in any part of the body. Particularly, since legs of the body are far distant from the heart and are largely affected by gravity, blood flow to the heart decreases, which causes edema. In addition, women may experience edema during normal pregnancy or preeclampsia, and when lots of moisture or salt is taken or when fatigued or unable to sleep, the edema may temporarily appear but will subside on its own. When capillary permeability is increased, for example, in case of burns, trauma, local inflammation, allergic reaction, and the like, the edema may locally occur. In particular, leg edema accompanies swelling of feet and ankles and thus may be easily recognized as a feeling of tight shoes, and in addition, since a swollen feeling of the legs accompanies a heavy feeling of the legs, fatigue of the whole body may be perceived as the leg edema. Systemic edema may be classified into cardiac, renal, hepatic, endocrine, and dystrophic edema, and local edema may be classified into edema due to occlusion of blood vessels and lymphatic vessels, vasomotor edema, etc. When the edema develops, there may be body swelling, weight gain, swollen eyes when waking up from sleep, tight rings on fingers, and tight shoes. When calf tibia is pressed with a finger, it may appear hollow and pitted edema. Edema is known to promote blood circulation disorders and skin aging due to local excessive moisture in the skin. In general, skin problems are known to exacerbate conditions of people having improper lymphatic functions and overloaded lymphedema.

The skin is in the closest contact with an external environment in the human body and is an important organ protecting the inside of the human body therefrom. The skin is largely classified into epidermis, dermis, and hypodermis. Herein, the hypodermis consists of fat cells forming adipose tissues storing energy as fat and playing a role of accumulating or releasing the energy in the body. In other words, the hypodermis is stored as triglycerides in adipocytes, when the energy is more supplied than demanded, and broken into free fatty acids and glucose when the energy is depleted.

On the other hand, recently in contemporary society, with improvement of living standards according to economic growth, obese population is rapidly increasing due to lack of exercise and a high protein diet, so more people are suffering from many diseases due to obesity. Accordingly, exercise therapy, diet therapy, drug therapy, etc. are being developed and conducted to treat the obesity in contemporary society.

However, the exercise therapy and the diet therapy may not be expected to have an appropriate effect on the obesity and obesity-related diseases of contemporary people who are busy with life, and moreover, fat cells, when they are once made, may be reduced in size but not naturally removed and permanently remain in the body. Accordingly, it may be appropriate to develop and use safe skin external preparations (e.g., ointments, cosmetics, and the like) that can help break down fat to accompany the therapies.

Therefore, the present inventors have confirmed that a compound represented by a specific chemical formula promotes production or activation of reelin and/or VEGF-C as an active ingredient, and further, thereby improves swelling, lymphedema, skin wrinkles, and obesity, completing the present invention.

SUMMARY

An embodiment is to provide a promoter that promotes reelin and VEGF-C production or activation.

Another embodiment provides a skin external composition using the promoter.

According to an embodiment, a reelin and/or VEGF-C production and/or activation promoter includes a compound including a sulfonic acid group and an amino group as an active ingredient.

The compound may include a sulfonic acid group at one terminal end and an amino group at the other terminal end of both terminal ends.

The compound may be represented by Chemical Formula 1.

[Chemical Formula 1]

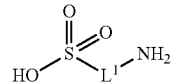

In Chemical Formula 1, $L^1$ is a substituted or unsubstituted C1 to C20 alkylene group or a substituted or unsubstituted C6 to C20 arylene group.

$L^1$ may be an unsubstituted C1 to C10 alkylene group.

The compound containing the sulfonic acid group and the amino group may be included in a concentration range of about 1 ppm to about 200 ppm based on the total amount of the reelin and/or VEGF-C production and/or activation promoter.

Another embodiment provides a skin external composition including the compound including a sulfonic acid group and an amino group as an active ingredient and improving swelling, lymphedema, skin wrinkles, or obesity by promoting reelin and/or VEGF-C production and/or activation.

The skin external composition may be an agent for improving swelling, and the swelling may be caused by abnormal formation of lymphatic vessels, dysfunction of lymphatic vessels, or both.

The skin external composition may be an agent for improving lymphedema, and the lymphedema may be caused by an abnormal formation of lymphatic vessels, dysfunction of lymphatic vessels, or both.

The skin external composition may be an anti-obesity agent, and the obesity may be caused by an abnormal formation of lymphatic vessels, dysfunction of lymphatic vessels, or both.

Another embodiment provides a method for improving swelling, lymphedema, skin wrinkles, or obesity by applying an effective amount of the reelin and/or VEGF-C production and/or activation promoter including the compound including a sulfonic acid group and an amino group, to the skin.

According to an embodiment, provided is a novel ingredient effective for preventing or controlling swelling, lymphedema, wrinkle formation, or obesity by inducing the expression of reelin and/or VEGF-C to activate the lymphatic function.

DETAILED DESCRIPTION OF THE EMBODIMENTS

Figure 1:
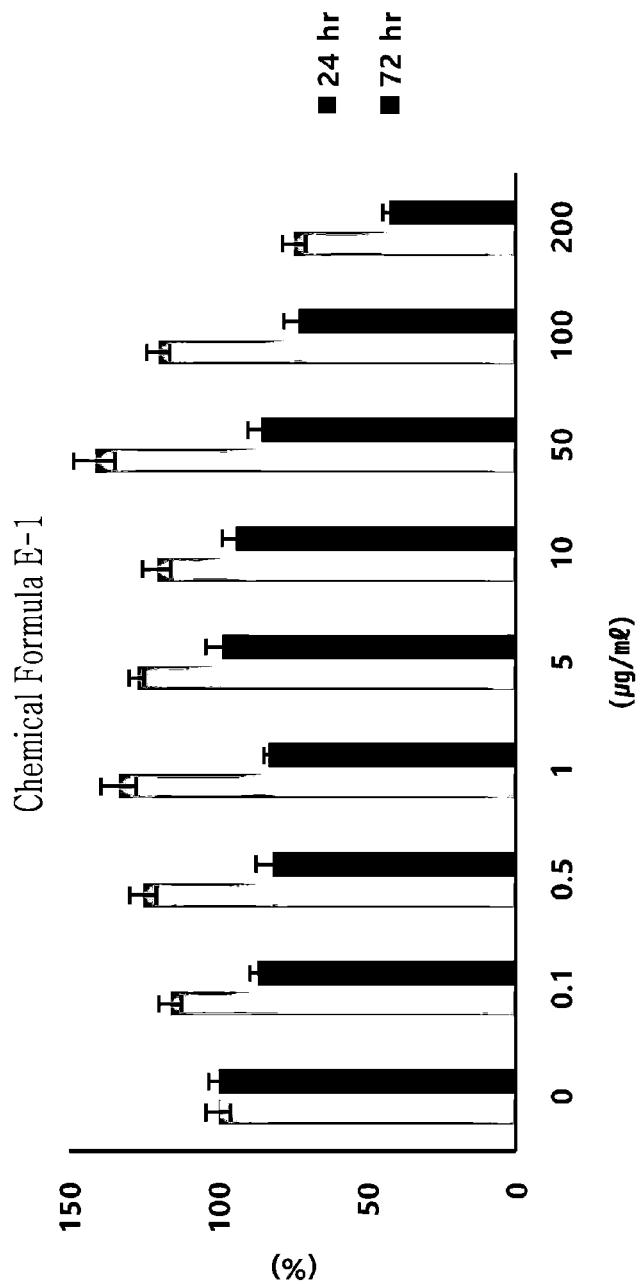
FIG. 1 is a graph showing the cytotoxicity experimental results of the compound represented by Chemical Formula E-1.

Hereinafter, example embodiments of the present disclosure will be described in detail. However, these example embodiments are only examples and do not limit the present disclosure. However, this disclosure may be embodied in many different forms and is not construed as limited to the example embodiments set forth herein.

As used herein, the term "reelin (RELN)" refers to an extracellular matrix-related molecule.

As used herein, when specific definition is not otherwise provided, "substituted" refers to replacement of at least one hydrogen of a functional group of the present disclosure by at least one substituent selected from a halogen atom (F, Br, Cl, or I), a hydroxy group, a nitro group, a cyano group, an amino group ($NH_2$, $NH(R^{200})$, or $N(R^{201})(R^{202})$, wherein $R^{200}$, $R^{201}$, and $R^{202}$ are the same or different and are each independently a 01 to 010 alkyl group), an amidino group, a hydrazine group, a hydrazone group, a carboxyl group, a substituted or unsubstituted alkyl group, a substituted or unsubstituted alkenyl group, a substituted or unsubstituted alkynyl group, a substituted or unsubstituted alicyclic organic group, a substituted or unsubstituted aryl group, and a substituted or unsubstituted heterocyclic group.

As used herein, when specific definition is not otherwise provided, "alkyl group" refers to a C1 to C20 alkyl group, and specifically a C1 to C15 alkyl group, "cycloalkyl group" refers to a C3 to C20 cycloalkyl group, and specifically a C3 to C18 cycloalkyl group, "alkoxy group" refers to a C1 to C20 alkoxy group, and specifically a C1 to C18 alkoxy group, "aryl group" refers to a C6 to C20 aryl group, and specifically a C6 to C18 aryl group, "alkenyl group" refers to a C2 to C20 alkenyl group, and specifically a C2 to C18 alkenyl group, "alkylene group" refers to a C1 to C20 alkylene group, and specifically a C1 to C18 alkylene group, and "arylene group" refers to a C6 to C20 arylene group, and specifically a C6 to C16 arylene group.

As used herein, when a definition is not otherwise provided, the term "combination" refers to mixing or copolymerization. Also, "copolymerization" refers to block copolymerization or random copolymerization, and "copolymer" refers to a block copolymer or random copolymer.

The skin vasculature resides within the dermis and consists of blood vessels and lymphatic vessels. In order to maintain homeostasis, tissue fluid that has moved out of the blood vessel must be refluxed back into the vein. The veins of the skin efficiently send blood flow to the center. However, the veins themselves lack ability to receive tissue fluid. Accordingly, tissues receiving the tissue fluid, that is, lymphatic vessels, are also an essential structure to the skin.

The lymphatic vessels play an important role in maintaining a constant state of microenvironment around cells by recovering water and proteins that are constantly leaking from unnecessary substances and blood vessels present in the skin. In addition, the lymphatic vessels have been thought to play a role in resisting infectious agents and foreign agents from outside through transport of T lymphocytes.

The lymphatic vessels are known to have symptoms such as swelling, lymphedema, and the like, which are lymphatic dysfunctions. In addition, the lymphatic vessels are not limited to swelling but are known to play an important role in photoaging (wrinkle formation) of the skin by ultraviolet (UV) rays.

Studies so far have identified VEGFR-3 as a transmembrane receptor, which is specifically present in the lymphatic vessels, and discovered VEGF-C and VEGF-D as its ligand. VEGF-C acts on the lymphatic vessels to promote proliferation, migration, and luminal cavity formation of lymphatic endothelial cells, thereby activating functions of the lymphatic vessels. In addition, VEGF-C is introduced into edema as a pathological condition of swelling to explore possible gene therapy.

In addition, in recent years, mice with genetic mutations that cause the dysfunction of lymphatic vessels are known to show obesity, when mature. With respect to a mechanism that formation and dysfunction of lymphatic vessels indicate obesity, lymph fluid flowing through the lymphatic vessels is known to promote differentiation of progenitor mast cells into fat. In other words, the lymphatic fluid has been reported to leak out of the lymphatic vessels due to dysfunction of the lymphatic vessels and thus differentiate the fat and furthermore form obesity. Accordingly, a VEGF-C promoter is expected as a therapeutic agent to prevent obesity that functionally regenerates the lymphatic vessels.

VEGF family genes exist from VEGF-A to VEGF-E. Among them, VEGF-B and VEGF-E have been identified as factors acting on blood vessels alone. VEGF-A is known to be present in the skin and act on the lymphatic vessels but on the contrary, worsen functions of the lymphatic vessels.

In the skin, VEGF-D is reported to exist in a very small amount in the dermis, but since knockout mice of VEGF-D do not cause abnormalities in formation and function of the lymphatic vessels, VEGF-D is considered to be not essential for the formation of the lymphatic vessels of the skin. On the other hand, mice with high expression of VEGF-C in the epidermis confirm that an increase in the number of the lymphatic vessels in the dermis indicates that VEGF-C in the skin is strongly expressed in the epidermis. As a result of blocking an effect of VEGF-C in the epidermis by highly expressing a neutralizing antibody of VEGFR-3, a receptor of VEGF-C, the number of lymphatic vessels in the dermis has been dramatically reduced (Makinen, T., Jussila, L., Veikkola, T., Karpanen, T., Kettunen, M. I., Pulkkanen, K. J., Kauppinen, R., Jackson, D. G., Kubo, H., Nishikawa, S., Yla-Herttuala, S. & Alitalo, K. 2001 Nat Med 7, 199-205). Accordingly, since functions of the lymphatic vessels in the skin dermis is controlled by VEGF-C expressed in the epidermis, VEGF-C is blocked from functioning, resulting in swelling (edema).

Furthermore, in recent years, various attempts have been made to control swelling or edema by activating or strengthening lymph or lymphatic vessels to control swelling or edema, improve skin aging (wrinkles), and prevent, suppress, and treat obesity, wherein the activation or strengthening of the lymph or the lymphatic vessels may also be achieved by promoting production, differentiation, and activity of reelin in addition to VEGF-C.

Accordingly, the present inventors have performed numerous experiments and trials and errors to find an active ingredient capable of improving swelling, lymphedema, skin wrinkles, or obesity by promoting the production or activity of reelin and/or VEGF-C and confirmed that a composition including a compound including a sulfonic acid group and an amino group as an active ingredient may function as a reelin and/or VEGF-C production and/or activation promoter, completing the present invention.

For example, the compound may include a sulfonic acid group at one terminal end and an amino group at the other terminal end of both terminal ends.

For example, the compound may be represented by Chemical Formula 1.

[Chemical Formula 1]

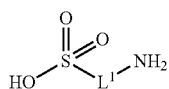

In Chemical Formula 1, $L^1$ is a substituted or unsubstituted C1 to C20 alkylene group or a substituted or unsubstituted C6 to C20 arylene group.

For example, in Chemical Formula 1, $L^1$ may be an unsubstituted C1 to C10 alkylene group.

For example, the compound represented by Chemical Formula 1 may be included in a concentration range of about 1 ppm to about 200 ppm, for example greater than or equal to about 1 ppm and less than or equal to about 200 ppm, less than or equal to about 190 ppm, less than or equal to about 180 ppm, less than or equal to about 170 ppm, less than or equal to about 160 ppm, less than or equal to about 150 ppm, less than or equal to about 140 ppm, less than or equal to about 130 ppm, less than or equal to about 120 ppm, less than or equal to about 110 ppm, less than or equal to about 100 ppm, less than or equal to about 90 ppm, less than or equal to about 80 ppm, less than or equal to about 70 ppm, less than or equal to about 60 ppm, less than or equal to about 50 ppm, less than or equal to about 40 ppm, less than or equal to about 30 ppm, less than or equal to about 20 ppm, for example about 1 ppm to about 10 ppm based on the total amount of the reelin and/or VEGF-C production and/or activation promoter.

The reelin and/or VEGF-C production and/or activation promoter according to an embodiment includes the compound including a sulfonic acid group and an amino group, for example the compound represented by Chemical Formula 1 as an active ingredient, and the concentration range is satisfied, thereby effectively promoting the formation and function of lymphatic vessels. Symptoms accompanying the dysfunction of the lymphatic vessels may include not only swelling and lymphedema, but also photoaging (wrinkle formation, etc.) of the skin caused by ultraviolet rays, obesity, and the like. The reelin and/or VEGF-C production and/or activation promoter according to one embodiment of the present disclosure may be effective in preventing and suppressing photoaging of the skin according to ultraviolet (UV) rays and obesity along with swelling or lymphedema. In addition, the reelin and/or VEGF-C production and/or activation promoter may also be effective in treating congenital lymphedema.

The photoaging of the skin means a change in appearance and function of the skin, which is generally confirmed as a result of repeated exposure to sunlight. Ultraviolet (UV) light, a component of the sunlight and particularly, moderate UV (called to be UVB, a wavelength of about 290 nm to about 320 nm), mainly causes the photoaging. An exposure dose of UVB required to cause the photoaging is currently unknown. However, repeated exposure to UVB at a level causing erythema or sunburn usually leads to the photoaging. Clinically, the photoaging may be specified as skin roughness, formation of wrinkles, pigmentation of spots, haemorrhage, formation of sagging, onset of telangiectasia, occurrence of moles, onset of purpura, susceptibility to scarring, atrophy, occurrence of a fibrotic pigment removal area, and premalignant and malignant tumors. The photoaging usually occurs on skin habitually exposed to sunlight such as the face, ears, head, neck, and hands.

According to an embodiment, a skin external composition for improving swelling, lymphedema, skin wrinkles, or obesity includes the compound including a sulfonic acid group and an amino group, for example the compound represented by Chemical Formula 1, as an active ingredient to promote reelin and/or VEGF-C production and/or activation.

For example, the skin external composition may be a swelling improving agent, and the swelling may be caused by abnormal formation of lymphatic vessels, dysfunction of lymphatic vessels, or both.

For example, the skin external composition may be an agent for improving lymphedema and the lymphedema may be caused by an abnormal formation of lymphatic vessels, dysfunction of lymphatic vessels, or both.

For example, the skin external composition may be an anti-obesity agent, and the obesity may be caused by an abnormal formation of lymphatic vessels, dysfunction of lymphatic vessels, or both.

It is possible to appropriately determine the dosage, application form, and formulation of the skin external composition according to the embodiment according to the purpose of use. For example, the compound represented by Chemical Formula 1 may be formulated at a concentration of about 1 ppm to about 10 ppm, for example about 1 ppm to about 5 ppm, for example about 5 ppm to about 10 ppm, for example about 2 ppm to about 9 ppm, for example about 3 ppm to about 8 ppm, relative to the total concentration of the skin external composition as an active ingredient. However, the present disclosure is not limited thereto. The form of application of the skin external composition is not particularly limited, and it can be applied both by inhalation and transdermally. The formulations may be any form, for example, perfumes, shampoos, conditioners, skin care, body shampoos, body conditioners, body powders, air fresheners, deodorants, bath agents, lotions, creams, soaps, toothpastes, cosmetics such as aerosol products, and other fragrances in general. It may also be used for medicines such as inhalation drugs.

In addition to the above essential ingredients, the skin external composition includes ingredients commonly used in skin external composition for example cosmetics and pharmaceuticals, for example whitening agents, moisturizing agents, antioxidants, oily ingredients, ultraviolet absorbers, surfactants, thickeners, alcohols, powder components, colorants, aqueous components, water, various skin nutrients, and the like may be appropriately blended as needed.

In addition, metal sequestering agents such as disodium edetate, trisodium edetate, sodium citrate, sodium polyphosphate, sodium metaphosphate, and gluconic acid, caffeine, tannin, verapamil, tranexamic acid and derivatives thereof, licorice extract, glabridean, hot water extract of quince fruit, various crude drugs, drugs such as tocopherol acetate, glycyrrhizic acid, and derivatives thereof, or salts thereof, vitamin C, magnesium ascorbate phosphate, ascorbyl glucoside, arbutin, whitening agents such as kojic acid, sugars, such as glucose, fructose, mannose, sucrose, and trehalose, vitamin A such as retinoic acid, retinol, retinol acetate, and retinol palmitate, and the like may also be further included suitably.

For example, the skin external composition may be a cosmetic composition.

In the present specification "cosmetic" may refer to any material that may have a medical function in addition to the cosmetic function, as well as the cosmetic function.

The chemical formulation of the cosmetic composition is not particularly limited and may be appropriately selected as desired.

For example, the cosmetic composition may be formulated into chemical formulations such as solutions, suspend liquid, emulsions, pastes, gels, creams, lotions, powders, soaps, surfactant-containing cleansings, oils, powder foundations, emulsion foundations, wax foundations, and sprays, but is not limited thereto. More specifically, it may be formulated into cosmetic compositions such as detergents, tonics, hair dressings, nourishing lotions, essences, serums, treatments, conditioners, shampoos, lotions, wools, or hair dyes, and the like, and may be formulated into basic cosmetics such as oil-in-water (O/W) type, water-in-oil (W/O), and the like. For example, the composition may have one formulation selected from skin lotion, skin toner, astringent, lotion, milk lotion, moisture lotion, nourishing lotion, massage cream, nourishing cream, moisture cream, hand cream, ointment, foundation, essence, nourishing essence, pack, soap, cleansing foam, cleansing lotion, cleansing cream, body lotion, body cleanser, gel, cream, patch, and spray. In addition, in the composition, in addition to the above-mentioned essential components in each chemical formulation, other components may be appropriately selected and formulated without difficulty by a person of ordinary skill in the art according to types or use purposes of other external preparations. For example, ultraviolet (UV) blocking agents, hair conditioning agents, fragrances, and the like may be further included.

The cosmetic composition may include a cosmetically acceptable medium or base. These are all chemical formulations suitable for topical applications. The cosmetic composition may be provided in the forms of emulsions obtained by dispersing an oil phase in an aqueous phase, suspensions, microemulsions, microcapsules, microgranules, or ion-type (liposome) and/or non-ionized vesicle dispersing agents or in the forms of creams, skins, lotions, powders, ointments, sprays, or concealed sticks. These compositions may be prepared according to conventional methods in the art.

When the chemical formulation of the present disclosure is a solution or emulsion, a solvent, a solubilizer, or an emulsifier may be used as carrier components. For example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid ester of sorbitan may be used.

If the chemical formulation of the present disclosure is a suspension, the carrier component may be a diluent of a liquid such as water, ethanol or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, tracant, and the like.

If the chemical formulation of the present disclosure is pastes, creams, or gels, the carrier component may be animal oil, vegetable oil, wax, paraffin, starch, tracant, cellulose derivatives, polyethylene glycol, silicone, bentonite, silica, talc, or zinc oxide.

If the chemical formulation of the present disclosure is powders or sprays, the carrier component may be lactose, talc, silica, aluminum hydroxide, calcium silicate, or polyamide powders. Particularly, in the case of sprays, a propellant such as chlorofluorohydrocarbon, propane/butane, or dimethyl ether may be additionally included.

In an embodiment of the present disclosure, it may include thickeners in addition to the cosmetic composition. The thickeners included in the cosmetic composition of the present disclosure may be methyl cellulose, carboxyl methyl cellulose, carboxyl methyl hydroxy guanine, hydroxy methyl cellulose, hydroxyethyl cellulose, carboxyl vinyl polymer, polyquaternium, cetearyl alcohol, stearic acid, and carrageenan. Preferably one or more of carboxyl methyl cellulose, carboxyl vinyl polymer, and polyquaternium may be used, and most preferably a carboxyl vinyl polymer may be used.

In an embodiment of the present disclosure, the cosmetic composition may include a variety of suitable bases and additives as needed, and the types and amounts of these components may be easily selected by the inventor. If necessary, it may include an acceptable additive, and may further include, for example, conventional ingredients such as antiseptics, pigments, additives, and the like.

The antiseptics may be specifically phenoxyethanol or 1,2-hexanediol, and the fragrances may be artificial flavors.

In an embodiment of the present disclosure, the cosmetic composition may include a composition selected from water-soluble vitamins, oil-soluble vitamins, polymeric peptides, polymeric polysaccharides, sphingolipids, and seaweed extracts. Other ingredients that may be added include fats and oils, humectants, emollients, surfactants, organic and inorganic pigments, organic powders, ultraviolet (UV) absorbers, antiseptics, fungicides, antioxidants, plant extracts, pH adjusters, alcohols, pigments. fragrances, blood circulation accelerators, coolants, anhidrotics, purified water, and the like.

In addition, the compounding components which may be added otherthan these are not limited thereto. Moreover, any component may be blended in the range which does not damage the purpose and effect of the invention.

Furthermore, the skin external composition according to an embodiment may be used as a pharmaceutical composition.

Advantages and features of the present disclosure and methods for achieving them will be apparent with reference to the examples described below in detail. One aspect of the present disclosure will be described in detail with reference to examples. However, these examples are specifically provided for describing the present disclosure, and the range of the present disclosure is not limited to these examples.

EXAMPLES

Experimental Example 1: Cytotoxicity Analysis

Human dermal lymphatic endothelial cells (HDLEC, PromoCell, Germany) were newly cultured in 96 well dishes for one day and then treated with a compound represented by Chemical Formula E-1 (Biogenics Company) at each concentration of 0 ppm (μg/mℓ) to 200 ppm (μg/mℓ). The cells were cultured for 24 hours and 72 hours, and then measured with respect to absorbance at 450 nm by using a QuantiMax WST-8 Cell viability assay kit to check cell viability, and the results are shown in FIG. 1.

[Chemical Formula E-1]

Referring to FIG. 1, the compound represented by Chemical Formula E-1 had no cytotoxicity within a concentration range of 200 ppm.

Experimental Example 2: Reelin Cytokine Analysis

Figure 2:
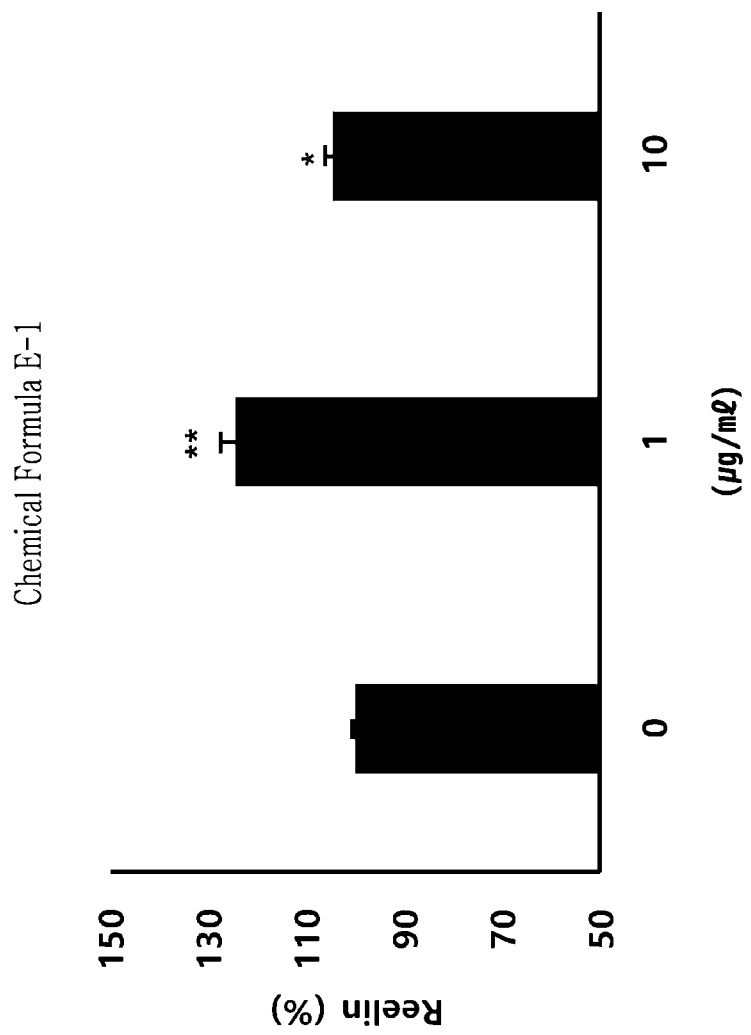
FIG. 2 is a graph showing the analysis results of the reelin cytokine of the compound represented by Chemical Formula E-1.

After culturing human dermal lymphatic endothelial cells in 6 well plates for 24 hours, while the cells with no treatment (N.T) were used as a reference (100%), the cells were treated with the compound represented by Chemical Formula E-1 at each concentration of 1 ppm and 10 ppm and cultured for 48 hours and then measured with respect to production and activity of reelin through a reelin cytokine analysis by using human reelin ELISA Kit (Mybiosource, U.S.A.) according to a manual, and the results are shown in FIG. 2.

Referring to FIG. 2, the cells treated with the compound represented by Chemical Formula E-1 turned out to further improve production and activity of reelin, compared with the cells with no treatment (control).

Experimental Example 3: VEGF-C Cytokine Analysis

Figure 3:
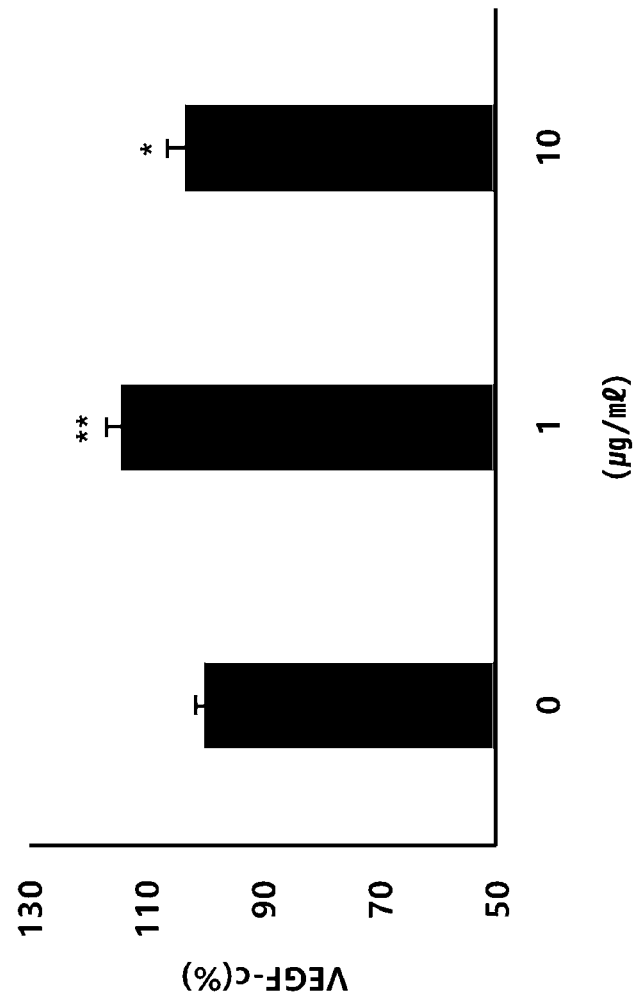
FIG. 3 is a graph showing the VEGF-C cytokine analysis results of the compound represented by Chemical Formula E-1.

After culturing human dermal lymphatic endothelial cells in 6 well plates for 24 hours, while the cells with no treatment (N.T) were used as a reference (100%), the cells were treated with the compound represented by Chemical Formula E-1 at each concentration of 1 ppm and 10 ppm and cultured for 48 hours and then measured with respect to production and activity of VEGF-C through a VEGF-C cytokine analysis by using a VEGFC human ELISA Kit (ThermoFisher, U.S.A.) according to a manual, and the results are shown in FIG. 3.

Referring to FIG. 3, the cells treated with the compound represented by Chemical Formula E-1 turned out to further improve production and activity of VEGF-C, compared with the cells with no treatment (control).

Experimental Example 4: Preparation of Skin External Composition

Cosmetic compositions having each composition shown in Table 1 and being usable as a skin external composition according to Example 1, Comparative Example 1 (mulberry leaf root extract; SK Bioland Co., Ltd.), and Comparative Example 2 (persimmon leaf extract; BIO-FD&C Co., Ltd.) were prepared. The cosmetic compositions were prepared by adding purified water in a balance amount to reach a total amount of 100 wt %, when summed with weights of the other components.

TABLE 1

(unit: ppm)

| | Example 1 | Comparative Example 1 | Comparative Example 2 |
|---|---|---|---|
| Purified water | balance | balance | balance |
| EDTA-2Na | 0.05 | 0.05 | 0.05 |
| Lauric acid | 5 | 5 | 5 |
| Myristic acid | 7 | 7 | 7 |
| Palmitic acid | 1 | 1 | 1 |
| KOH | 7.9 | 7.9 | 7.9 |
| Guar hydroxypropyl trimonium chloride | 0.5 | 0.5 | 0.5 |
| Polyquaternium-7 | 3.0 | 3.0 | 3.0 |
| Compound represented by Chemical Formula E-1 | 5.0 | — | — |
| Mulberry leaf extract | — | 5.0 | — |
| Persimmon leaf extract | — | — | 5.0 |
| Disodium cocoamphodiacetate | 1.0 | 1.0 | 1.0 |

After selecting 30 women having edema in lower leg calves over the age of 50 and instructing them to apply the compositions according to Example 1 and Comparative Examples 1 and 2 on the swollen lower leg calf area twice a day for 7 consecutive days, each of them was asked to measure i) change in weight (using a scale), ii) change in circumference length of the calf where it was the most swollen, and iii) state of swelling (examined with naked eyes), and the results are shown in Table 2.

TABLE 2

| | Example 1 | Comparative Example 1 | Comparative Example 2 |
|---|---|---|---|
| Weight (0 day) (kg) | 53 | 56 | 55 |
| Weight (7 days) (kg) | 53 | 57 | 55 |
| Calf circumference (0 day) (cm) | 35 | 37 | 36 |
| Calf circumference (7 days) (cm) | 34 | 37 | 36 |
| Edema condition | relieved | no change | no change |

From Table 2, it can be confirmed that when the skin external composition according to an embodiment is prescribed, the edema condition is relieved within a week compared to the case where it is not.

Although the preferred embodiments of the present disclosure have been described in detail, the scope of the present disclosure is not limited thereto, and various modifications and improvements by those skilled in the art using the basic concept of the present invention defined in the following claims are also within the scope of the invention.

What is claimed is:

1. A method for improving swelling, lymphedema, skin wrinkles, or obesity by applying an effective amount of the reelin and/or VEGF-C production and/or activation promoter comprising a compound of the following Chemical Formula 1 to skin of a subject:

Chemical Formula 1
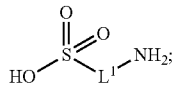
wherein, in Chemical Formula 1,
$L^1$ is a substituted or unsubstituted C1 to C20 alkylene group or a substituted or unsubstituted C6 to C20 arylene group.
2. The method of claim 1, wherein
$L^1$ is an unsubstituted C1 to C10 alkylene group.
* * * * *